United States Patent
Tsukuda

Patent Number: 6,038,020
Date of Patent: Mar. 14, 2000

[54] MASK PATTERN VERIFICATION APPARATUS EMPLOYING SUPER-RESOLUTION TECHNIQUE, MASK PATTERN VERIFICATION METHOD EMPLOYING SUPER-RESOLUTION TECHNIQUE, AND MEDIUM WITH PROGRAM THEREOF

[75] Inventor: Eiji Tsukuda, Hyogo, Japan

[73] Assignee: Mitsubishi Denki Kabushiki Kaisha, Tokyo, Japan

[21] Appl. No.: 09/158,526

[22] Filed: Sep. 22, 1998

[30] Foreign Application Priority Data

Mar. 27, 1998 [JP] Japan .................................. 10-080905

[51] Int. Cl.[7] .............................. G01N 21/00; G03F 9/00
[52] U.S. Cl. .................................. 356/237.5; 356/237.1; 356/237.2; 356/376; 430/5
[58] Field of Search ................................ 430/5, 302, 320; 355/78, 54; 382/8, 56; 356/237.1, 237.4, 237.5, 237.6, 237.2, 388, 376, 390, 445, 448

[56] References Cited

U.S. PATENT DOCUMENTS

| | | | |
|---|---|---|---|
| 4,445,776 | 5/1984 | Hyatt | 355/78 |
| 5,086,477 | 2/1992 | Yu et al. | 382/8 |
| 5,246,800 | 9/1993 | Muray | 430/5 |
| 5,340,700 | 8/1994 | Chen et al. | 430/312 |
| 5,441,834 | 8/1995 | Takekuma et al. | 430/5 |
| 5,565,285 | 10/1996 | Takekuma et al. | 430/5 |
| 5,725,971 | 3/1998 | Moriuchi et al. | 430/5 |

FOREIGN PATENT DOCUMENTS 8-334888  12/1996  Japan .

OTHER PUBLICATIONS

"Mathematical and CAD Framework for Proximity Correction", N. Cobb et al., SPIE Symposium on Microlithography '96, Mar. 1996, Santa Clara, CA, pp. 1–15.

"Vector Aerial Image with Off–Axis Illumination", E. Barouch et al., SPIE vol. 1927 Optical/Laser Microlithography VI(1993) pp. 686–695.

*Primary Examiner*—Frank G. Font
*Assistant Examiner*—Roy M. Punnoose
*Attorney, Agent, or Firm*—McDermott, Will & Emery

[57] ABSTRACT

A mask pattern verification apparatus includes a semiconductor circuit layout unit for generating layout data from semiconductor circuit data, a super-resolution corresponding pattern verification unit for verifying a pattern of the layout data generated by the semiconductor circuit layout unit according to a pitch with a line width and a space width, an optical simulation unit carrying out optical simulation on an error site of a pitch detected by the super-resolution corresponding pattern verification unit to output light intensity, and a contour output unit for generating and providing a contour according to the light intensity output from the optical simulation unit.

3 Claims, 12 Drawing Sheets

MASK PATTERN VERIFICATION APPARATUS EMPLOYING SUPER-RESOLUTION TECHNIQUE, MASK PATTERN VERIFICATION METHOD EMPLOYING SUPER-RESOLUTION TECHNIQUE, AND MEDIUM WITH PROGRAM THEREOF

BACKGROUND OF THE INVENTION

1. Field of the Invention

The present invention relates to a verification apparatus of a mask in a lithography process used in semiconductor fabrication, and more particularly, to a mask pattern verification apparatus employing super-resolution technique, a mask pattern verification method thereof, and a medium in which a program thereof is recorded.

2. Description of the Background Art

As semiconductor integrated circuit devices are scaled to higher densities, the necessity of microminiaturization of the pattern formed on a mask has become higher. However, there is limitation in the improvement of the resolution in microminiaturization. The super-resolution technique is now used in addition to the method of reducing the wavelength of the light source to effect microminiaturization. For example, the Levenson method and the modified illumination method are known such super-resolution technique.

In the Levenson method, the resolution of the pattern formed on a mask is improved for microminiaturization by arranging a phase shifter on the mask. In the modified illumination method, the resolution of the pattern formed on the mask is improved for microminiaturization by altering the configuration of the light source per se. The usage of the super-resolution technique allows a finer pattern to be formed on the mask.

In these few years, optical simulation has been employed for the purpose of estimating the final configuration of a pattern formed on a mask. FIG. 1 is a flow chart for describing the procedure of correcting a layout employed in conventional optical simulation. First, layout data is produced from the semiconductor circuit data generated by the circuit design (S101). In producing the layout data, the line width and the space width (exposure dimension) are prevented from taking a value smaller than a predetermined value. Then, mask data for use with optical simulation is generated from the produced layout data. Optical simulation is performed according to a predetermined optical condition (S102). By this optical simulation, the pattern that will be actually formed on a mask can be evaluated.

The user verifies the layout by referring to the result of the optical simulation (S103). For example, the user visually verifies the final configuration displayed on a screen. When the final configuration of the displayed pattern is not appropriate, the layout is corrected (S104), and the process from the optical simulation (S102) onward is repeated. After eliminating any defect in the final configuration of the pattern, a mask is formed.

As an alternative to the manual verification of step S103, the layout data can be corrected automatically employing OPC (Optical Proximity Correction) shown in FIGS. 2A and 2B. At the corner of a pattern, there is an area that cannot be irradiated sufficiently with the light. OPC is directed to approximate the final configuration to the desired configuration by expanding the area of the layout pattern that is not subjected to sufficient light, as shown in FIGS. 2A and 2B.

In correcting the layout employing the conventional optical simulation, the range that can be verified visually is limited. There was a problem that the verification of the entire layout was extremely time-consuming.

Furthermore, in the event of correcting the layout pattern by OPC, it was necessary to visually check whether the corrected result is proper or not. In other words, the layout subjected to OPC must be subjected to optical simulation again in order to verify the layout after the OPC shown in FIGS. 2A and 2B. The result of the optical simulation had to be verified again visually.

In the conventional layout verification system, it is difficult to correct the layout since it does not accommodate the super-resolution technique. Although the line width and the space width can be reduced than the level allowed according to the conventional resolution limit by employing the super-resolution technique, there is a phenomenon where the final line or space becomes larger or smaller at a certain dimension region. It was difficult to identify that certain dimension region and provide a process compensating for this phenomenon. It was difficult to estimate the final configuration of a mask pattern.

SUMMARY OF THE INVENTION

An object of the present invention is to provide a mask pattern verification apparatus that can easily verify a mask pattern generated by super-resolution technique, and that can correct the layout at high accuracy.

Another object of the present invention is to provide a mask pattern verification apparatus that can easily verify a mask pattern generated by super-resolution technique and that can automatically correct the layout.

A further object of the present invention is to provide a mask pattern verification method that can easily verify a mask pattern generated by super-resolution technique and that can correct the layout at high accuracy.

Still another object of the present invention is to provide a mask pattern verification method that can easily verify a mask pattern generated by super-resolution technique and that can automatically correct the layout.

A still further object of the present invention is to provide a medium in which is recorded a mask pattern verification program that can easily verify a mask pattern generated by super-resolution technique and that can correct the layout at high accuracy.

Yet a further object of the present invention is to provide a medium in which is recorded a mask pattern verification program that can easily verify a mask pattern generated by resolution technique and that can automatically correct the layout.

According to an aspect of the present invention, a mask pattern verification apparatus includes a semiconductor circuit layout unit for generating layout data from semiconductor circuit data, a super-resolution corresponding pattern verification unit for verifying the pattern of layout data generated by the semiconductor circuit layout unit according to a pitch with the line width and the space width, an optical simulation unit carrying out optical simulation of an error site of the pitch detected by the super-resolution corresponding pattern verification unit to output light intensity, and a contour output unit to generate a contour according to the light intensity from the optical simulation unit for output.

Since the super-resolution corresponding pattern verification unit verifies the pattern of the layout data generated by the semiconductor circuit layout unit according to a pitch including a line width and the space width, the layout data pattern corresponding to the super-resolution technique can be verified.

According to another aspect of the present invention, a mask pattern verification apparatus includes a semiconductor circuit layout unit for generating layout data from semiconductor circuit data, a hole corresponding verification unit for verifying a hole of the layout data generated by the semiconductor circuit layout unit from the position relationship with an adjacent pattern, an optical simulation unit for carrying out optical simulation of an error site of the hole detected by the hole corresponding verification unit to output light intensity, and a contour output unit to generate a contour according to the light intensity from the optical simulation unit for output.

Since the hole corresponding verification unit verifies a hole in the layout data generated by the semiconductor circuit layout unit from the position relationship with an adjacent pattern, a hole corresponding to super-resolution technique can be verified.

According to a further aspect of the present invention, a mask pattern verification apparatus includes a semiconductor circuit layout unit for generating layout data from semiconductor circuit data, an optical simulation unit for carrying out optical simulation on the layout data generated by the semiconductor circuit layout unit to output light intensity, a contour output unit to generate a contour according to the light intensity from the optical simulation unit for output, a distortion verification unit for verifying a distortion in the contour output from the contour output unit according to the layout data generated by the semiconductor circuit layout unit, and a layout correction unit for correcting the layout data according to the distortion verification result by the distortion verification unit.

Since the distortion verification unit detects a distortion of a contour output from the contour output unit according to the layout data generated by the semiconductor circuit layout unit, the error site of the layout data can be verified automatically.

According to still another aspect of the present invention, a mask pattern verification method includes the steps of generating layout data from semiconductor circuit data, detecting an error site of a pitch of a pattern of the layout data generated according to a pitch with a line width and a space width, carrying out optical simulation on the detected error site of the pitch to output light intensity, and generating and providing a contour according to the output light intensity.

Since the error site of the pitch of the generated layout data pattern is detected according to the pitch including the line width and the space width, the mask pattern corresponding to the super-resolution technique can be verified.

According to a still further aspect of the present invention, a mask pattern verification method includes the steps of generating layout data from semiconductor circuit data, detecting an error site of a hole of the generated layout data from the position relationship with an adjacent pattern, carrying out optical simulation on the detected error site of the hole to output light intensity, and generating and providing a contour according to the output light intensity.

Since the error site of a hole is detected from the position relationship of the pattern adjacent to the hole of the generated layout data, a hole corresponding to the super-resolution technique can easily be verified.

According to yet a further aspect of the present invention, a mask pattern verification method includes the steps of generating layout data from semiconductor circuit data, carrying out optical simulation on the generated layout data to output light intensity, generating and providing a contour according to the output light intensity, verifying a distortion of the output contour according to the generated layout data, and correcting the layout data according to the verification result.

Since the distortion of the contour is verified according to the generated layout data, layout data verification can be carried out automatically, not manually.

According to yet another aspect of the present invention, a mask pattern verification program recorded on a medium includes the steps of generating layout data from semiconductor circuit data, detecting an error site of a pitch of a pattern of the generated layout data according to a pitch with a line width and a space width, carrying out optical simulation on the detected error site of the pitch to output light intensity, and generating and providing a contour according to the output light intensity.

Since the pitch error site of the pattern of the generated layout data is detected according to the pitch including the line width and the space width, verification of a mask pattern corresponding to the super-resolution technique can be easily carried out.

According to yet a still further aspect of the present invention, a mask pattern verification program recorded on a medium includes the steps of generating layout data from semiconductor circuit data, detecting an error site of a hole of the generated layout data from the position relationship with an adjacent pattern, carrying out optical simulation on the detected error site of the hole to output light intensity, and generating and providing a contour according to the output light intensity.

Since the error site of the hole can be detected from the position relationship of a pattern adjacent to the generated layout data hole, a hole corresponding to the resolution technique can easily be verified.

According to an additional aspect of the present invention, a mask pattern verification program recorded on a medium includes the steps of generating layout data from semiconductor circuit data, carrying out optical simulation on the generated layout data to output light intensity, generating and providing a contour according to the output light intensity, verifying a distortion in a contour output according to the generated layout data, and correcting the layout data according to the verification result.

Since the distortion of a contour is verified according to the generated layout data, layout data verification can be implemented automatically, not manually.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 3:
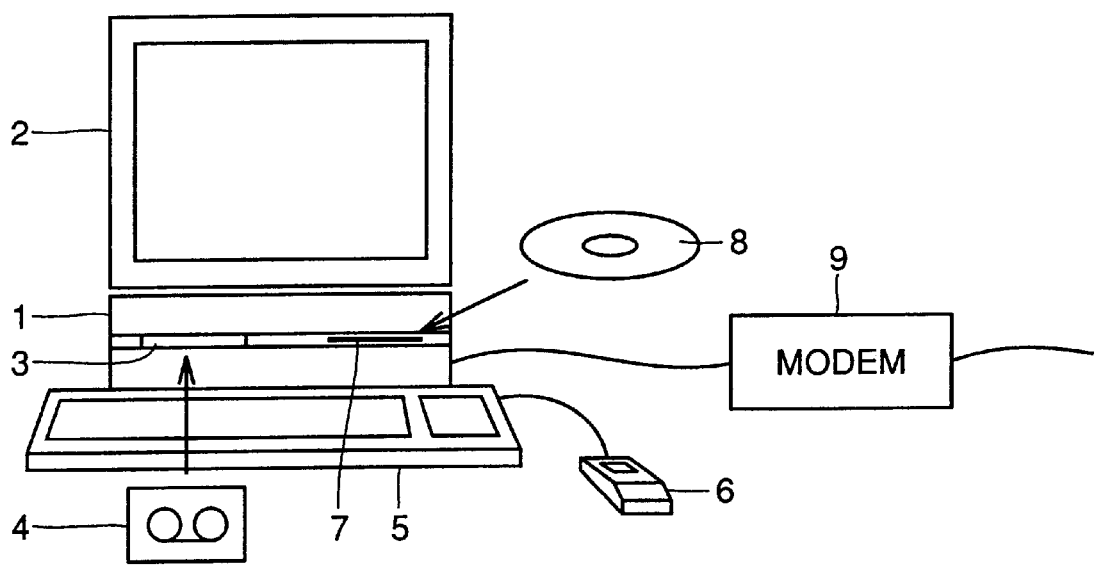
FIG. 3 shows an appearance of a mask pattern verification apparatus of the present invention.

FIG. 3 shows the appearance of a mask pattern verification apparatus of the present invention. The mask pattern verification apparatus includes a computer unit 1, a graphic display device 2, a magnetic tape device 3 to which a magnetic tape 4 is attached, a keyboard 5, a mouse 6, a CD-ROM (Compact Disk-Read Only Memory) device 7 to which a CD-ROM 8 is attached, and a communication modem 9. As will be described afterwards, a mask pattern verification program is supplied through a recording medium such as magnetic tape 4 or CD-ROM 8. The mask pattern verification program is executed by computer unit 1. The operator manipulates keyboard 5 or mouse 6 to verify the mask pattern while viewing graphic display device 2. The mask pattern verification pattern may be supplied to computer unit 1 via communication modem 9 from another computer through a communication line.

Figure 4:
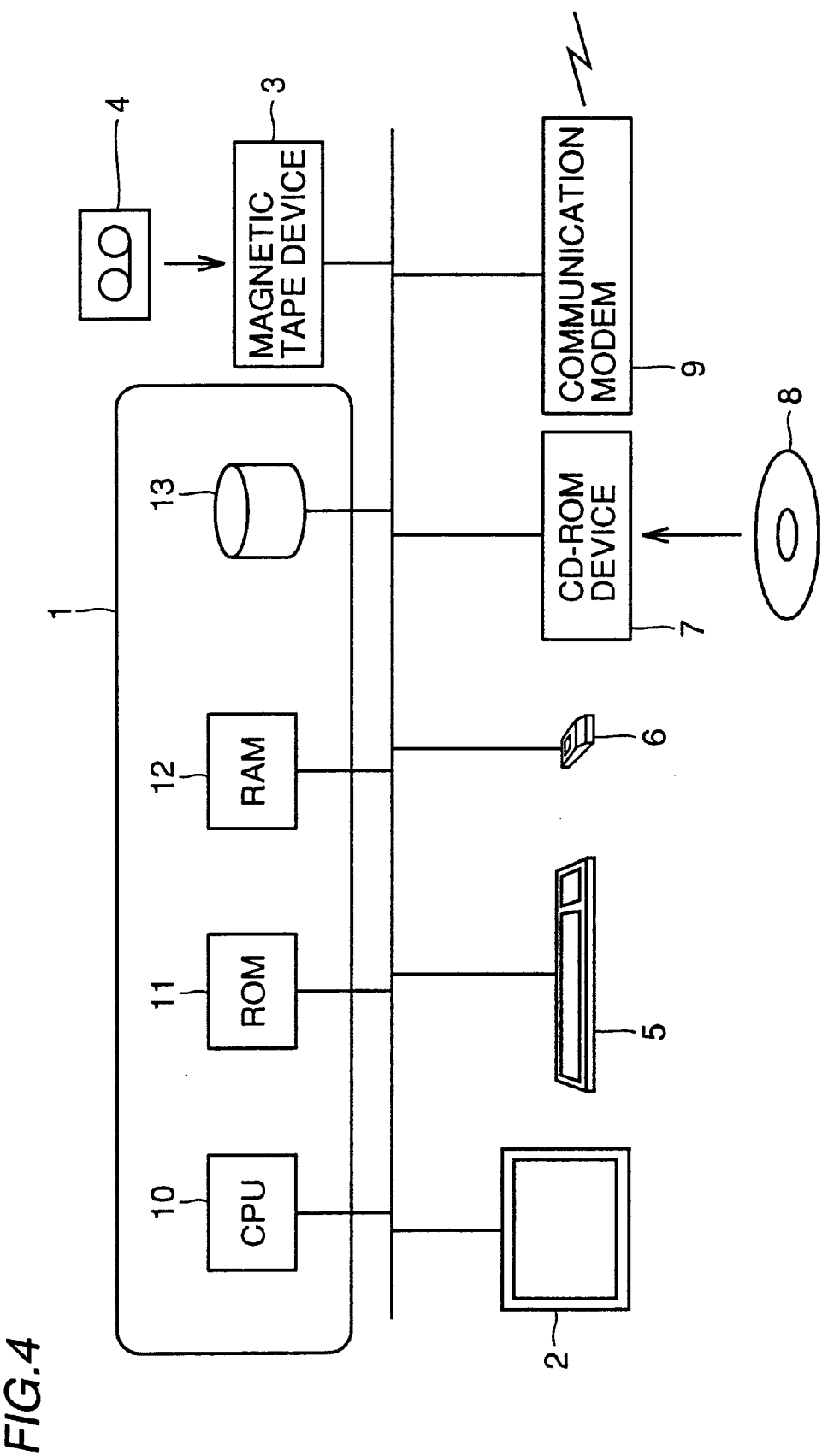
FIG. 4 is a block diagram showing a structure of a mask pattern verification apparatus according to the present invention.

FIG. 4 is a block diagram showing a structure of a mask pattern verification apparatus of the present invention. Computer unit 1 shown in FIG. 3 includes a CPU (Central Processing Unit) 10, a ROM (Read Only Memory) 11, a RAM (Random Access Memory) 12, and a hard disk 13. CPU 10 carries out a process while transferring data among graphic display device 2, magnetic tape device 3, keyboard 5, mouse 6, CD-ROM device 7, communication modem 9, ROM 11, RAM 12 or hard disk 13. The mask pattern verification program recorded in magnetic tape 4 or CD-ROM 8 is temporarily stored in hard disk 13 by CPU 10 through magnetic tape device 3 or CD-ROM device 7. CPU 10 carries out mask pattern verification by appropriately loading and executing the mask pattern verification program from hard disk 13 to RAM 12. Although the mask pattern verification apparatus of various embodiments of the present invention will be described hereinafter, it is to be noted that the appearance of the mask pattern verification apparatus shown in FIG. 3 and the structure block diagram of the mask pattern verification apparatus shown in FIG. 4 are common to each embodiment.

First Embodiment

Figure 5:
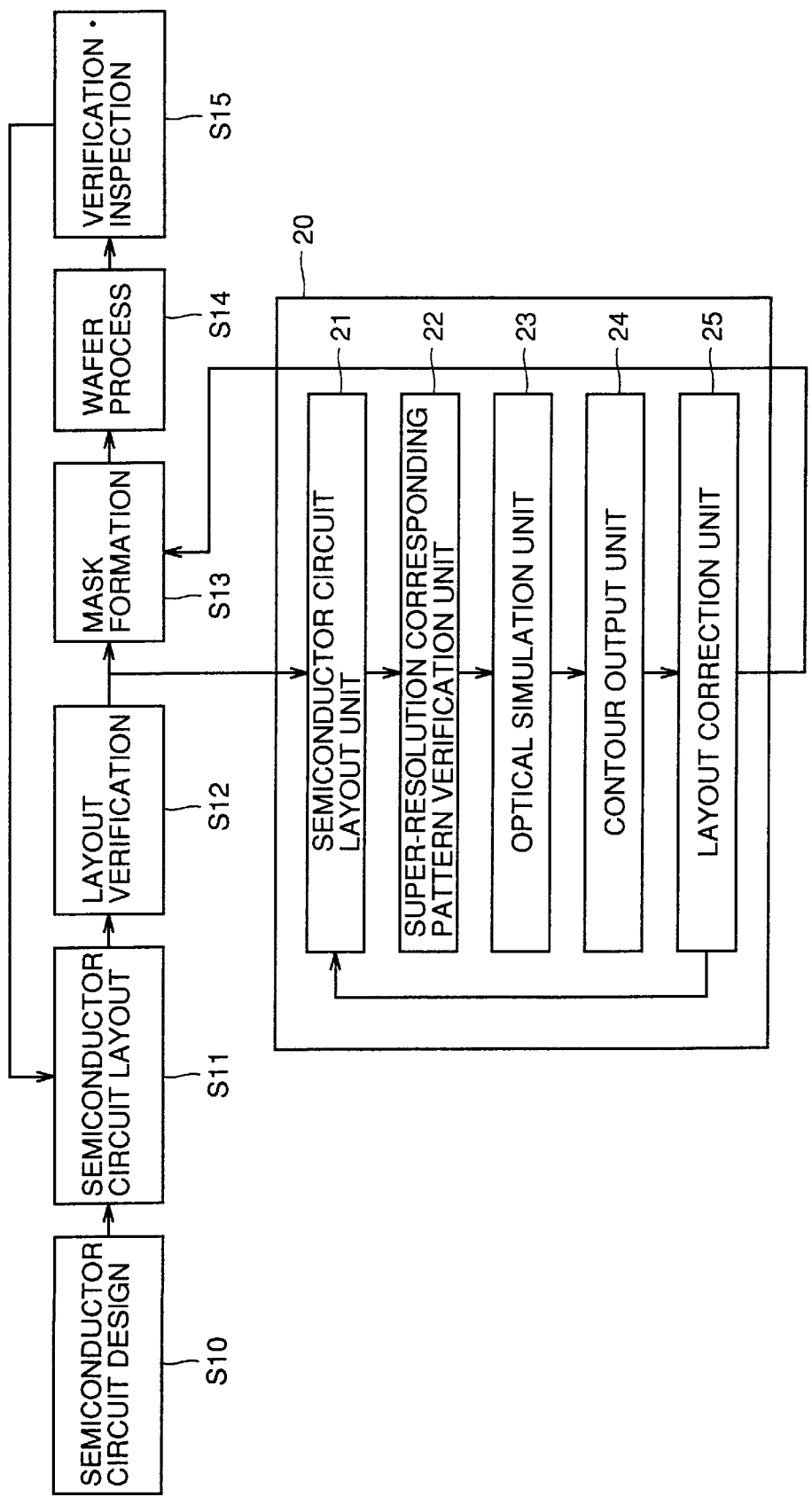
FIG. 5 is a diagram for describing a schematic structure of a mask pattern verification apparatus according to a first embodiment of the present invention and a procedure of mask verification using this mask pattern verification apparatus.

Referring to FIG. 5, a mask pattern verification apparatus 20 includes a semiconductor circuit layout unit 21 for generating layout data from semiconductor circuit data generated by a circuit design, a super-resolution corresponding pattern verification unit 22 for verifying a mask pattern corresponding to super-resolution technique, an optical simulation unit 23 for carrying out optical simulation according to layout data after verification by super-resolution corresponding pattern verification unit 22, a contour output unit 24 for generating and providing a contour according to light intensity output from optical simulation unit 23, and a layout correction unit 25 for the user to correct the layout by referring to the contour output from contour output unit 24.

Prior to describing in detail the mask pattern verification apparatus, verification of a mask pattern using mask pattern verification apparatus 20 will be described. First, the user provides a design of a semiconductor circuit (S10). A semiconductor circuit layout is generated from the semiconductor circuit data (S11). The user carries out layout verification such as DRC (Design Rule Check) on the generated layout data. If there is an error site, the layout is corrected. This layout verification does not correspond to the super-resolution technique, and is implemented by DRC described in the section of the background art.

The user verifies the layout corresponding to super-resolution technique with mask pattern verification apparatus 20. If there is an error site, that layout data is corrected. Then a mask is formed (S13). A wafer process is carried out using the generated mask (S14). The generated semiconductor is verified and inspected (S15). If it is necessary to correct the mask pattern, the procedure returns to step S11 to carry out the semiconductor circuit layout process again. By repeating this process, a mask corresponding to super-resolution technique can be formed.

Figure 6:
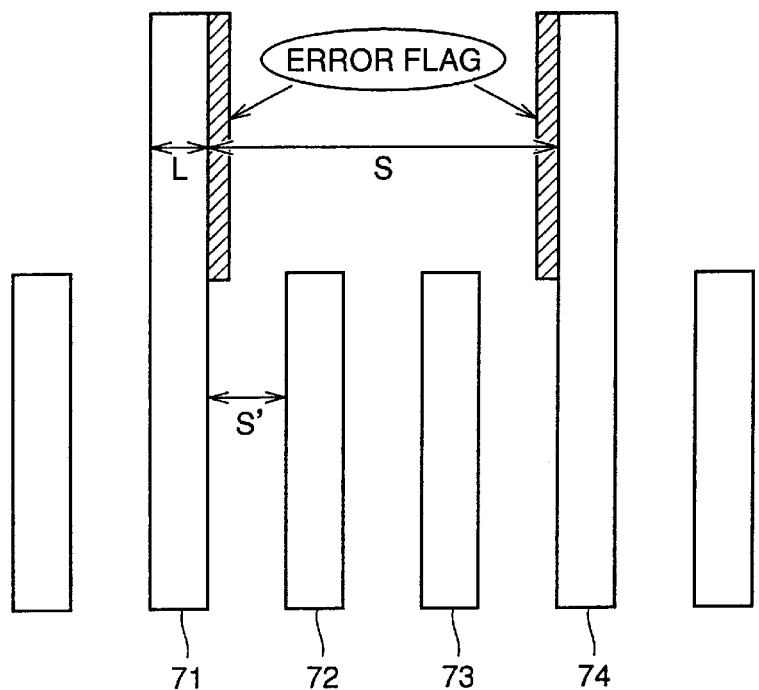
FIG. 6 is a diagram for describing a line width, a space width, and a pitch width of a mask pattern.

FIG. 6 is a diagram for describing pattern verification corresponding to super-resolution technique. In the conventional DRC not corresponding to super-resolution technique, the smallest values of a width L of, for example, line 71, and a space width S' between, for example, lines 71 and 72, are defined, wherein any line or space that is smaller than the relevant minimum value is output as an error site. In super-resolution technique, determination is made whether a pattern is correct or not by the value of a pitch width in addition to the definition of a line width and a space width. This pitch width includes one set of the line width and the space width. More specifically, this pitch width is, for example, the width L of line 71 shown in FIG. 6 plus the space width S between lines 71 and 74 (L+S), or the width L of line 71 plus the space width S' between lines 71 and 72 (L+S').

Figure 7:
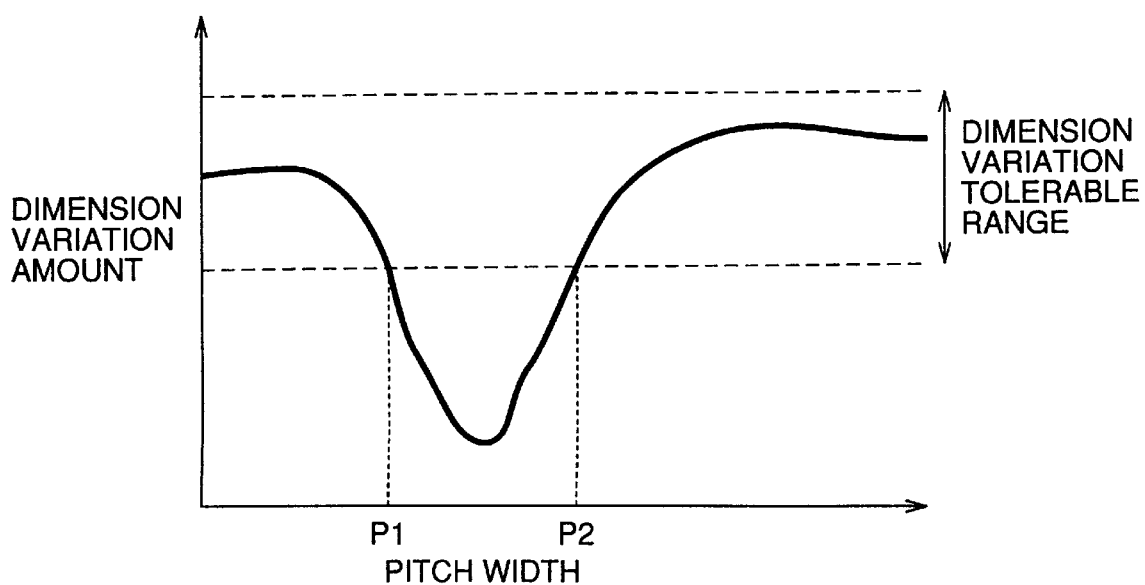
FIG. 7 is a diagram for describing the relationship between the pitch width and the error site of a mask pattern generated by super-resolution technique.

When the pitch width is varied with a fixed line width (when the space width is gradually increased or decreased), there is a possibility of an error site even in the region that does not show an error under the conventional DRC rule. More specifically, as shown in FIG. 7, there is a case where the dimension variation amount of the line width exceeds the tolerable range when the dimension of the line width that is fixed is altered in the event that the pitch width is gradually increased and the pitch width attains a certain constant value. In FIG. 7, the dimension variation amount of the line width exceeds the dimension variation tolerable range between P1 and P2. This pitch width is detected as an error site. This error site is output as an error flag shown in FIG. 6 as the hatched region. The same applies to the case where the pitch width is varied with a fixed space width or when the line width and the space width are both varied at the same time.

Figure 8:
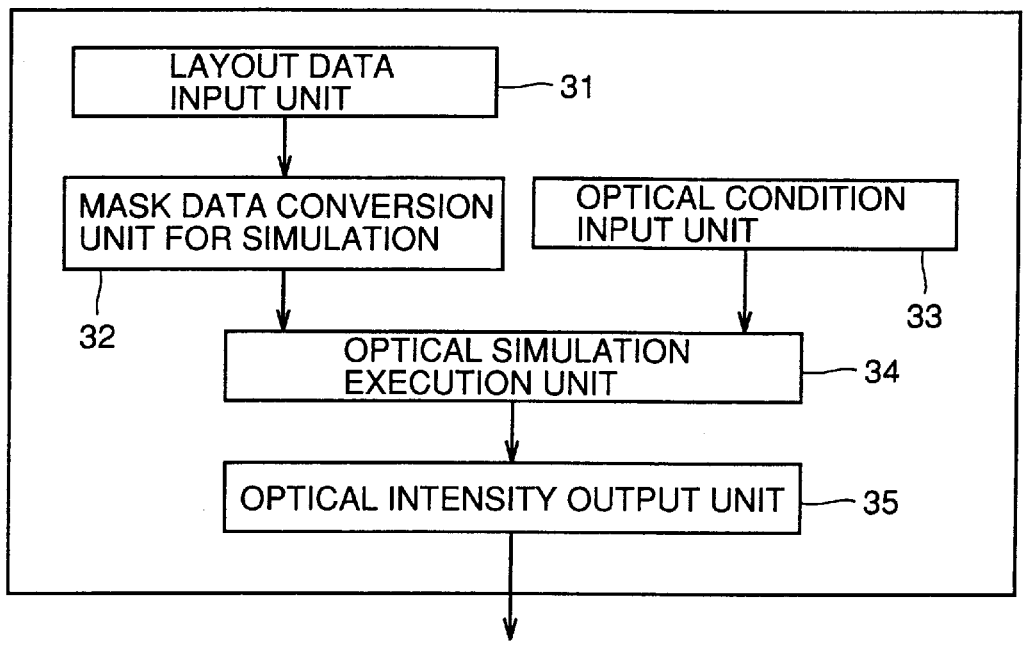
FIG. 8 is block diagram showing a schematic structure of an optical simulation unit 23 of FIG. 5.

FIG. 8 is a block diagram showing the schematic structure of optical simulation unit 23. Optical simulation unit 23 includes a layout data input unit 31 to which layout data is input, a mask data conversion unit 32 for use with simulation to convert layout data into mask data for optical simulation, an optical condition input unit 33 to which the optical condition actually used in the stepper is input, an optical simulation execution unit 34 for carrying out optical simulation according to the simulation mask data and optical condition to output light intensity, and a light intensity output unit 32 for providing light intensity which is the simulation result of optical simulation execution unit 34.

Figure 9:
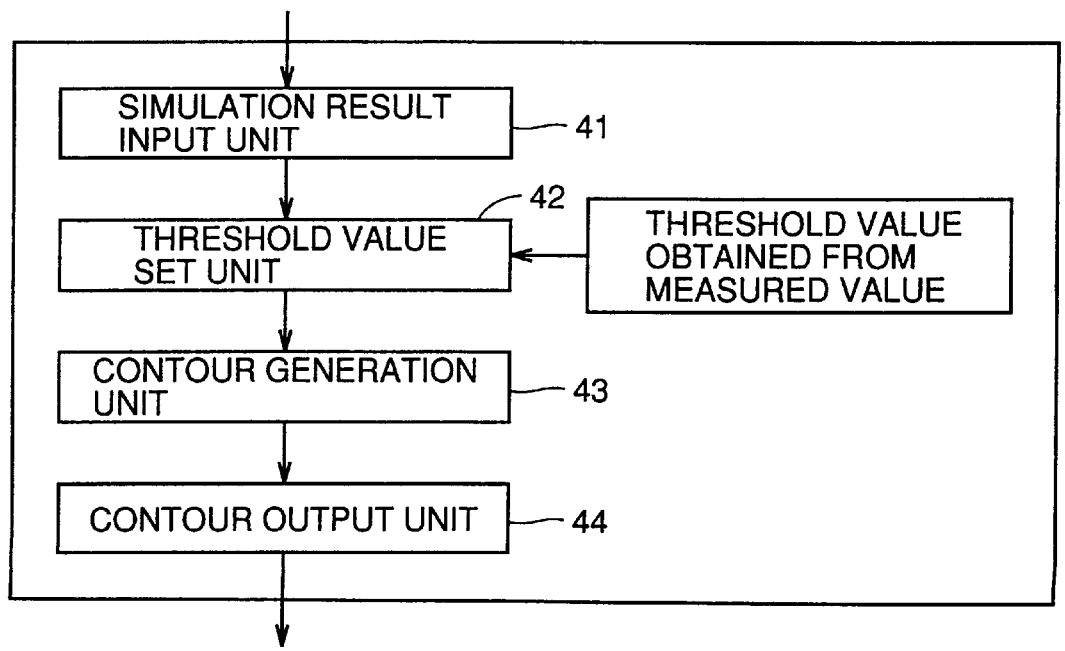
FIG. 9 is a block diagram showing a schematic structure of a contour output unit 24 of FIG. 5.

Referring to FIG. 9, contour output unit 24 includes a simulation result input unit 41 to which the light intensity from optical simulation unit 23 is input, a threshold value set unit 42 setting the threshold value of light intensity obtained by actual measurement, a contour generation unit 43 for generating a contour from the light intensity output from optical simulation unit 23 and the threshold value set by threshold value set unit 42, and a contour output unit 44 for providing the contour generated by contour generation unit 43. The contour generated by contour generation unit 43 represents the final configuration of the mask pattern evaluated from the optical simulation result (light intensity). This contour is represented by the isointensity line and the like of light intensity. The value of 0.3 is often employed as the threshold value.

Figure 10:
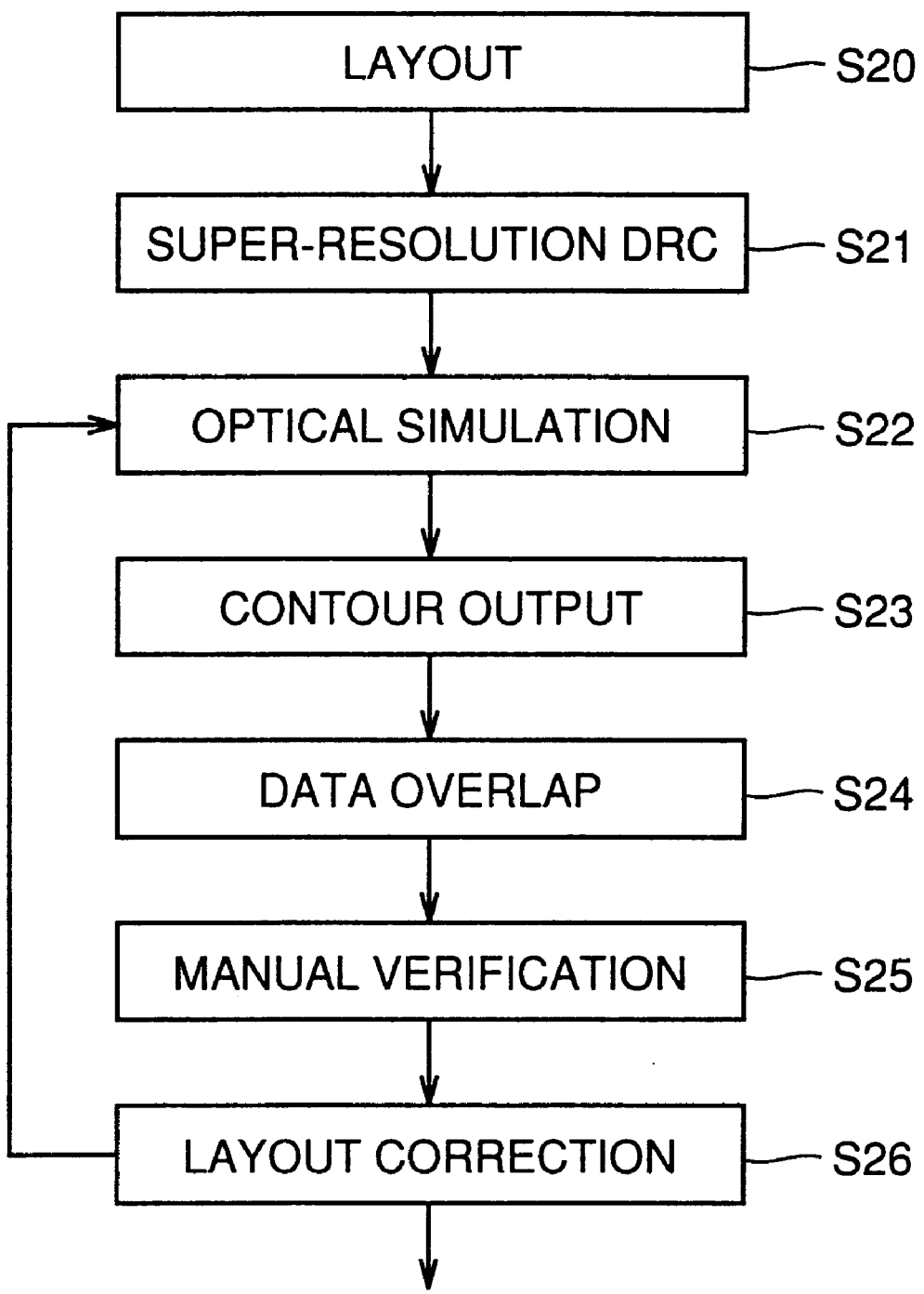
FIG. 10 is a flow chart for describing the procedure of a mask pattern verification apparatus according to the first embodiment of the present invention.

The processing procedure of mask pattern verification apparatus 20 will be described hereinafter with reference to the flow chart of FIG. 10. First, layout data is generated from the circuit data by semiconductor circuit layout unit 21 (S20). Verification of the pattern is carried out by super-resolution corresponding pattern verification unit 22 using the super-resolution DRC described with reference to FIGS. 6 and 7 (S21). Here, super-resolution corresponding pattern verification unit 22 provides a display so that the region where the dimension variation amount is outside the tolerable range can be identified as the error site. The user refers to this error site to determine whether this region is improper or not. There is a possibility that the pattern cannot be modified or that the detected error site is where accuracy is not particularly required depending upon the neighborhood of the error site. In the case where the error site is deficient, optical simulation is carried out for only that site (S22).

Contour output unit 24 generates a contour from the light intensity output from optical simulation unit 23. An overlapping display is provided of the generated contour and the original geometric layout. The user can confirm how great the final configuration of the mask pattern is offset from the original geometric layout by referring to the display. The area of the overlapping display of the contour and the original geometric layout is only a portion of the entire mask. Therefore, it will not take so much time for the user to visually verify the display. When the user makes a judgement that the layout must be corrected, the relevant site of the layout is corrected by layout correction unit 25 (S26).

Then, the program returns to step S22 to repeat the above-described process.

According to the mask pattern verification apparatus of the present embodiment, the mask pattern generated by super-resolution technique can easily be verified. Thus, the layout can be corrected at high accuracy.

Second Embodiment

Figure 11:
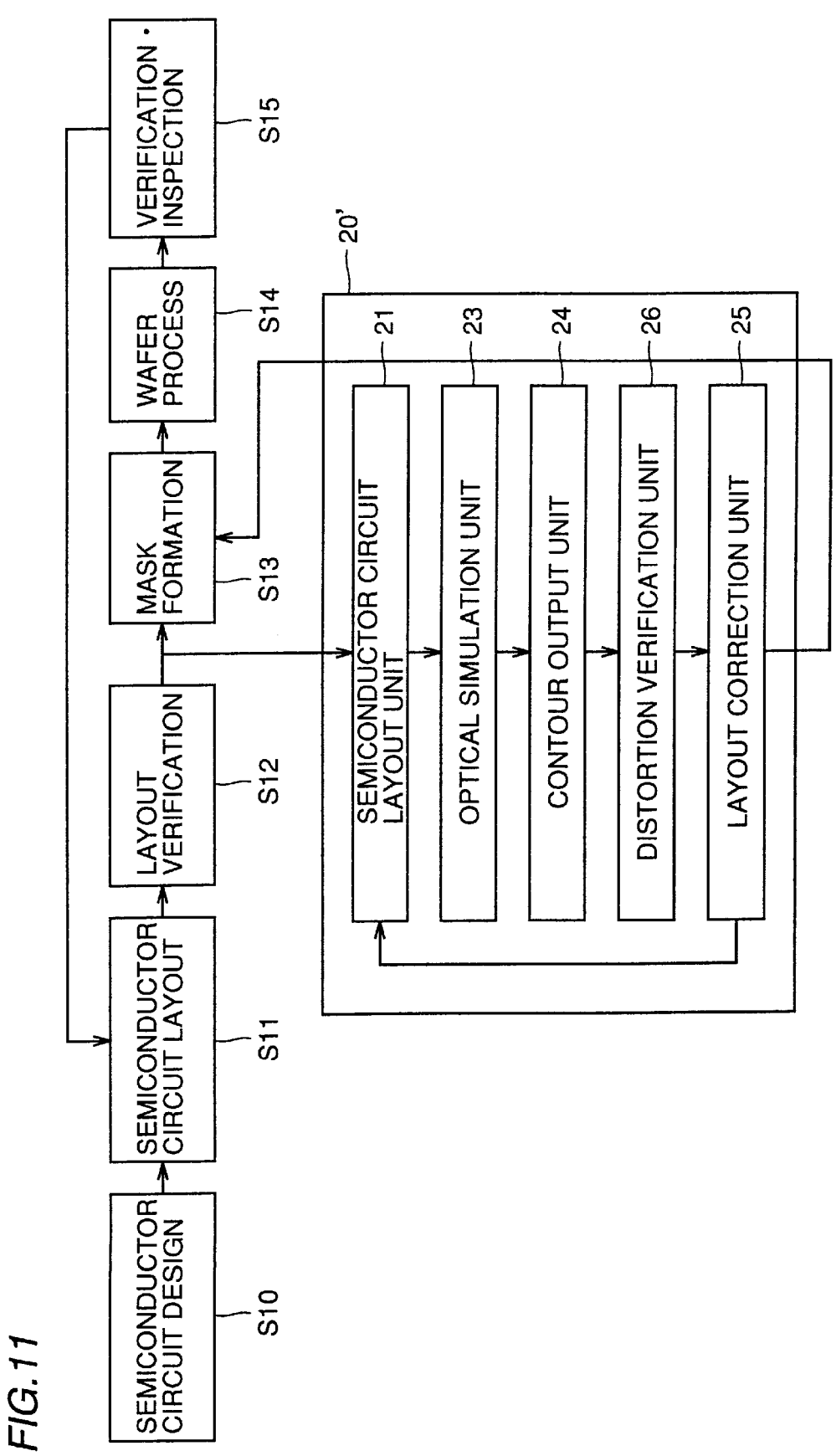
FIG. 11 is a diagram for describing a schematic structure of a mask pattern verification apparatus according to a second embodiment of the present invention and a procedure of mask verification using this mask pattern verification apparatus.

FIG. 11 shows a schematic structure of a mask pattern verification apparatus according to a second embodiment of the present invention and a processing procedure for generating a mask using this mask pattern verification apparatus. The mask pattern verification apparatus of the present embodiment differs from the mask pattern verification apparatus of the first embodiment shown in FIG. 5 in that super-resolution corresponding pattern verification unit 22 is absent, and that a distortion verification unit 26 is added between contour output unit 24 and a layout correction unit 25. Description of similar or corresponding components and functions will not be repeated.

Figure 12:
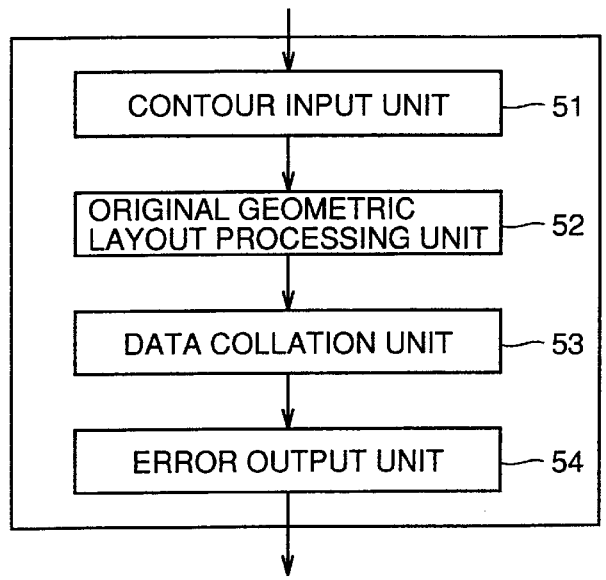
FIG. 12 is a block diagram showing a schematic structure of a distortion verification unit 26 of FIG. 11.

Referring to FIG. 12, distortion verification unit 26 includes a contour input unit 51 for entering a contour output from contour output unit 24, an original geometric layout processing unit 52 for generating an oversized and undersized geometric design from the original geometric layout, a data collation unit 53 to overlap an original geometric layout with an oversized geometric design and undersized geometric design generated from the original geometric layout for collation, and an error output unit 54 for providing the error detected by data collation unit 53.

Figure 13:
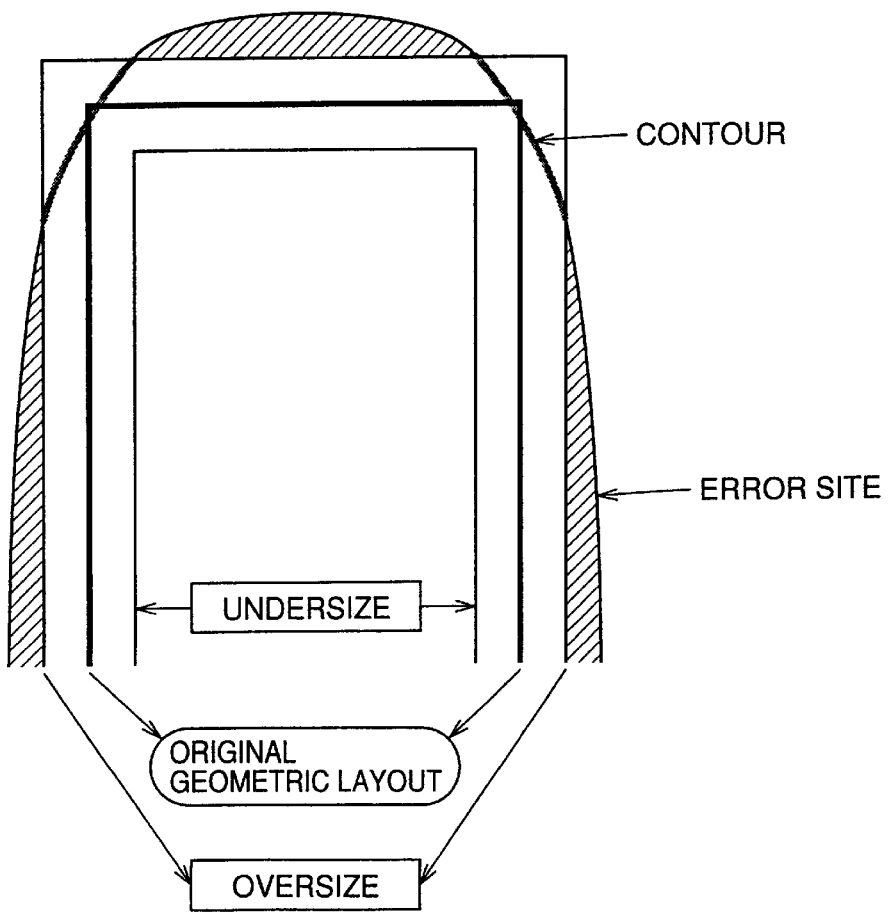
FIG. 13 is a diagram for describing distortion verification of a contour.

FIG. 13 is a diagram for describing the collation by data collation unit 53. Data collation unit 53 overlaps the undersized geometric design and the oversized geometric design generated from the original geometric layout with the contour to output the area of the contour that is outside the range of the undersized geometric design and the oversized geometric design as the error site. The hatched area in FIG. 13 corresponds to this error site. In contrast to the mask pattern verification apparatus of the first embodiment in which verification of an error site was effected visually by the user, the mask pattern verification apparatus of the present embodiment allows automatic verification by distortion verification unit 26.

Figure 14:
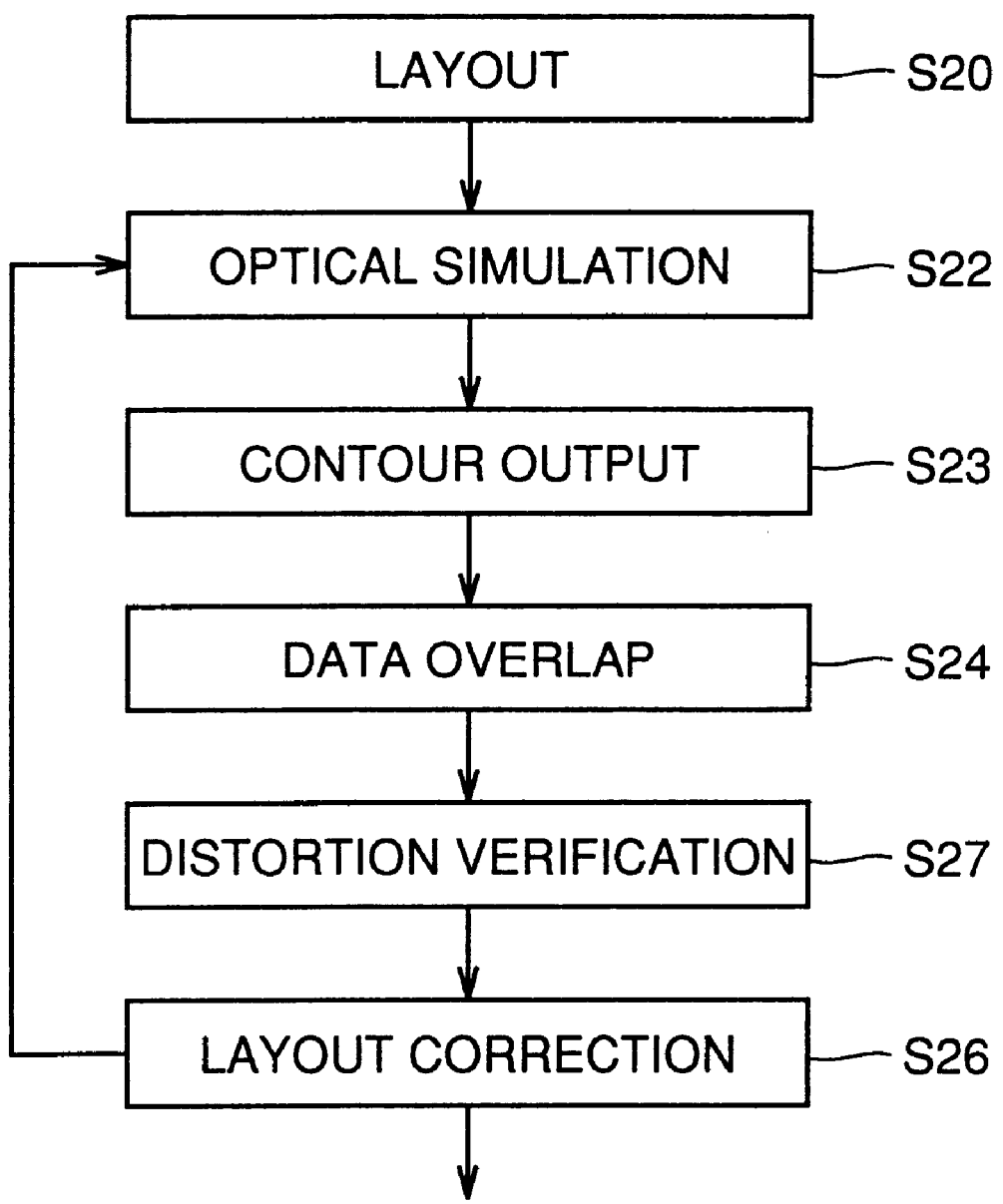
FIG. 14 is a flow chart for describing the procedure of the mask pattern verification apparatus of the second embodiment.

FIG. 14 is a flow chart for describing the processing procedure of the mask pattern verification apparatus of the present invention. First, semiconductor circuit layout unit 21 generates and provides layout data from the input semiconductor circuit data (S20). Optical simulation unit 23 carries out optical simulation on the entire region of the layout data output from semiconductor circuit layout unit 21 (S22). Contour output unit 24 generates and provides a contour from the light intensity output from optical simulation unit 23 (S23). Distortion verification unit 26 overlaps the contour with the undersized and oversized geometric designs as shown in FIG. 13 (S24). Distortion in the contour is verified by detecting an error site that is hatched in FIG. 13 (S27). By referring to the error site output from distortion verification unit 26, the user corrects the layout through layout correction unit 25 (S26). The optical simulation is carried out again with the corrected layout (S22). By repeating the above process, layout correction is effected.

If the contour is directly compared with the original geometric layout, a complex rule of an extremely high level is required to detect the error site from such a comparison since the contour has a smooth and complex shape. This is not applicable for practical usage. It is therefore appreciated that the above-described distortion verification by distortion verification unit 26 is a very effective method for verification.

At the corner area of the mask pattern, the final shape of the pattern is relatively rounded. There is a possibility that an area that is actually not an error is detected as an error site. This pseudo error can be reduced by altering the rule corresponding to the corner of the pattern to prevent an area to be erroneously detected as an error site.

According to the mask pattern verification apparatus of the present embodiment, verification of a mask pattern generated by super-resolution technique can be easily implemented with respect to the full chip. Layout verification can be carried out automatically. Since distortion verification can be carried out using the function of the general DRC, verification can be carried out at extremely high speed.

Third Embodiment

Figure 15:
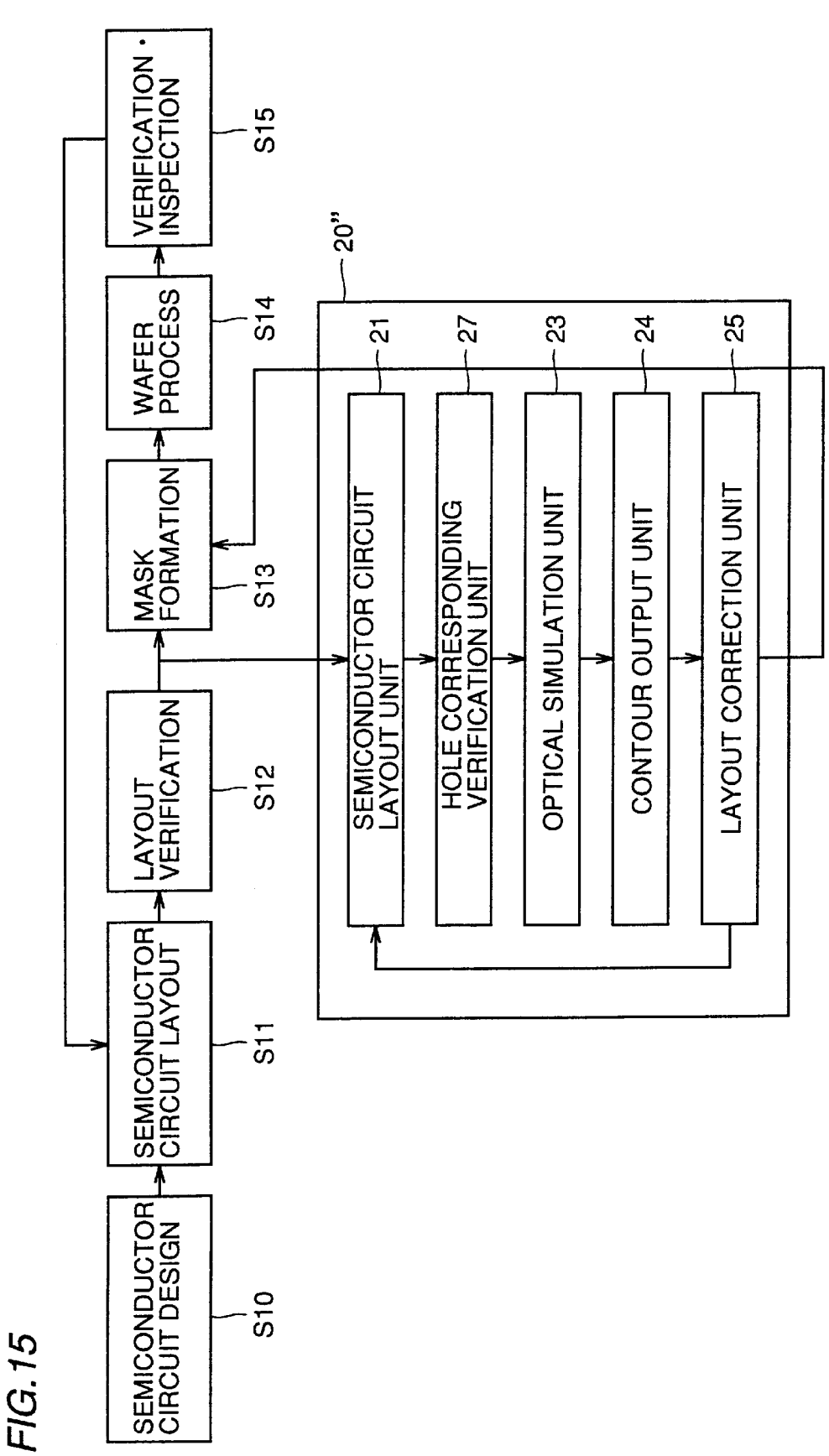
FIG. 15 is a diagram for describing a schematic structure of a mask pattern verification apparatus according to a third embodiment of the present invention and a mask verification procedure using this mask pattern verification apparatus.

FIG. 15 shows a schematic structure of a mask pattern verification apparatus according to a third embodiment of the present invention and the processing procedure of mask verification using this mask pattern verification apparatus. A mask pattern verification apparatus 20" according to the third embodiment differs from the mask pattern verification apparatus of the first embodiment shown in FIG. 5 in that super-resolution corresponding pattern verification unit 22 is substituted with a hole corresponding verification unit 27. Therefore, description of corresponding or similar components and functions will not be repeated. Regarding holes of a mask pattern generated by the super-resolution technique, there are cases where an error site occurs on the mask between holes depending upon the arrangement of adjacent holes. Hole corresponding verification unit 27 is directed to verify an error site according to the arrangement of these holes.

Figure 16:
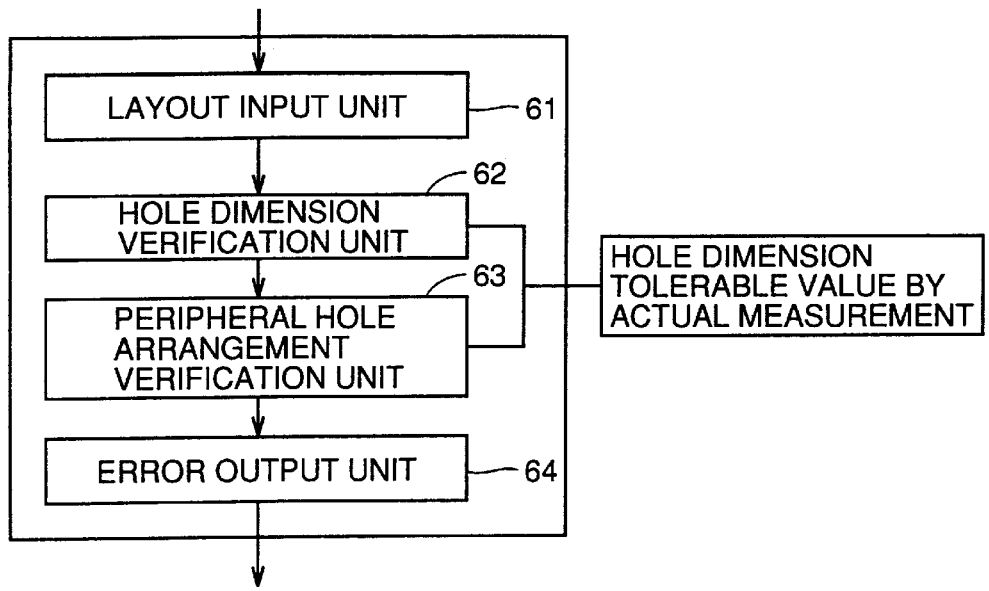
FIG. 16 is a block diagram showing a schematic structure of a hole corresponding verification unit 27 of FIG. 15.

FIG. 16 is a block diagram showing a schematic structure of hole corresponding verification unit 27. Hole corresponding verification unit 27 includes a layout input unit 61 to which the layout data generated by semiconductor circuit layout unit 21 is input, a hole dimension verification unit 62 to extract a hole to be verified from the layout data for verifying the dimension of that hole according to a predetermined rule, a peripheral hole arrangement verification unit 63 for carrying out verification according to the arrangement of the pattern around the hole to be verified and the distance between the relevant hole and the surrounding pattern, and an error output unit 64 for providing the extracted error site.

Hole dimension verification unit 62 carries out verification according to a predetermined rule of the minimum dimension of a hole as well as detecting the area outside the dimension variation tolerable range as an error site according to a pitch width defined by the width of a hole and the space width from another pattern, similar to the verification method of super-resolution corresponding pattern verification unit 22 described with reference to FIG. 6.

Figure 17:
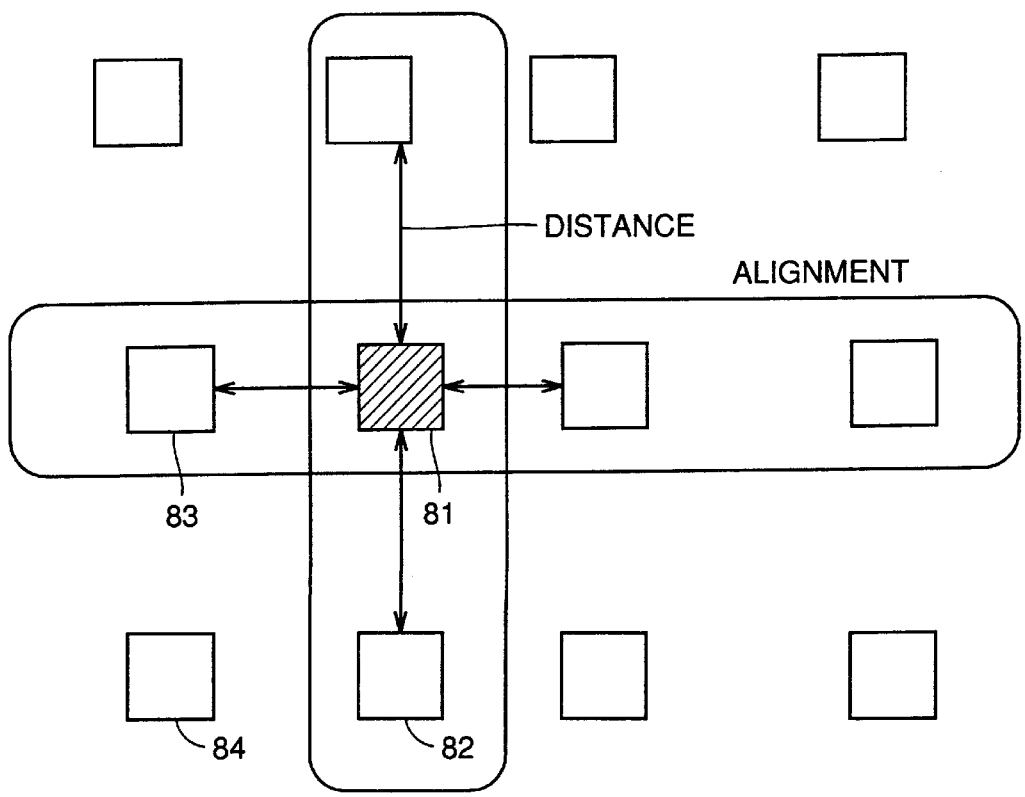
FIG. 17 is a diagram for describing verification of a hole generated by super-resolution technique.

FIG. 17 is a diagram for describing a verification method of peripheral hole arrangement verification unit 63. In super-resolution technique, particularly in employing the phase shifting method, there is a case where an erroneous pattern is formed in the proximity of the center area of holes 81, 82, 83 and 84 in the formation of the pattern of FIG. 17. For the purpose of preventing generation of such an error site, a rule defining the distance from four patterns adjacent to, for example, hole 81, is employed to output a site that is not within the tolerable range as an error site. Here, the employed rule uses a hole dimension tolerable value obtained by actual measurement.

According to the mask pattern verification apparatus of the present embodiment, a mask pattern corresponding to super-resolution technique for a hole-type pattern in addition to a line-type pattern can be easily verified. Thus, layout correction of higher accuracy is allowed.

Fourth Embodiment

The mask pattern verification apparatus of the fourth embodiment is similar in structure to the mask pattern verification apparatus of the first embodiment shown in FIG. 5. Only the function of threshold value set unit 42 in contour output unit 24 shown in FIG. 9 differs. The threshold value set unit is designated 42' in the mask pattern verification apparatus of the fourth embodiment. Description of similar or corresponding components and functions will not be repeated.

The most simplest method of setting a threshold value is set forth in the following. First, a pattern corresponding to the smallest dimension among the patterns is extracted. An actual measurement value is obtained so that the final pattern is achieved in fidelity. The actual measured value is set as the threshold value. This threshold value is used in all the other patterns. The final dimension of all the patterns is determined by this threshold value. According to this method, a contour can be verified in a short period of time. Although the final accuracy is not so good, this is of no particular problem in practical usage employing the currently available high sensitive resist. It can be said that -this method is effective as a part of the verification method corresponding to super-resolution technique.

However, there is a possibility that the accuracy is degraded if the threshold value of the light intensity is constant for all the patterns when the pattern is of a further fine dimension. In order to eliminate this problem, the threshold value is determined for each pattern employing the correlation between the actual measured value of the final pattern resist and the light intensity at the pattern edge portion evaluated by light intensity calculation. Threshold value set unit 42' sets a threshold value for each pattern in generating a contour. Although the time required for verification will become longer by this method, the completion of higher accuracy can be expected. Therefore, this method is particularly suitable for evaluating the patterns of small regions. According to the method of the present embodiment, dimension estimation and verification of a pattern including the resist effect are allowed. Pattern correction of high accuracy can be carried out for the detected error site.

Also, pattern verification of higher accuracy is allowed for completion of a pattern by etching according to a method similar to that of the above-described resist. Furthermore, a verification apparatus of high accuracy indispensable of actual measurement of the mask can be developed by estimating the completion of a resist by three-dimensional simulation.

According to the mask pattern verification apparatus of the present embodiment, the final mask pattern corresponding to a resist and etching can easily be verified. Thus, correction of the layout of higher accuracy is allowed.

Fifth Embodiment

A mask pattern verification apparatus according to a fifth embodiment of the present invention differs from the mask pattern verification apparatus of the second embodiment shown in FIG. 11 only in the function of layout correction unit 25. Therefore, description of similar or corresponding components and functions will not be repeated. The layout correction unit of the present embodiment is designated 25'.

Figure 1:
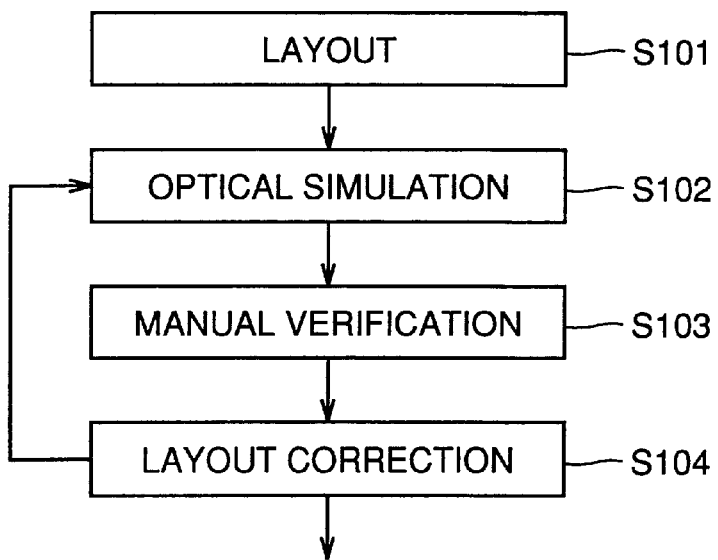
FIG. 1 is a flow chart for describing a method of verifying a mask pattern employing conventional optical simulation.
Figure 2A:
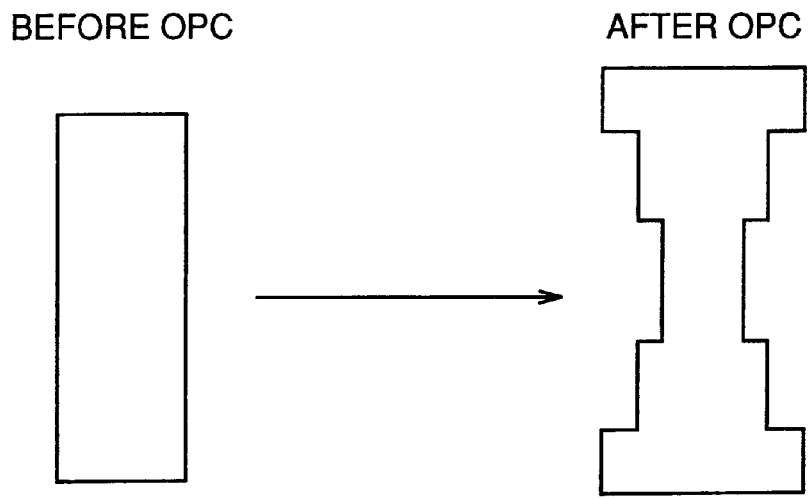
FIGS. 2A and 2B are diagrams for describing correction of a mask pattern using OPC.
Figure 2B:
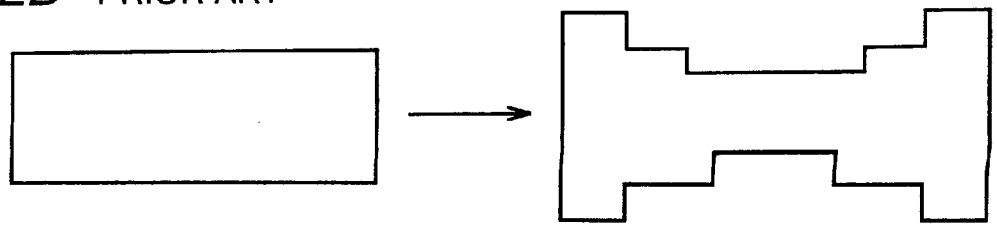

Layout correction unit 25' corrects the error site output from distortion verification unit 26 employing the OPC described with reference to FIGS. 2A and 2B. Since the pattern is corrected using the OPC, the user does not have to correct the layout. Mask pattern verification apparatus 20' can carry out all the processes automatically.

According to the mask pattern verification apparatus of the present embodiment, a mask pattern generated by super-resolution technique can be easily verified. Also, the layout can be corrected automatically.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A mask pattern verification method comprising the steps of:

generating layout data from semiconductor circuit data;

detecting an error site of a pitch of a pattern of said generated layout data according to a pitch including a line width and a space width;

carrying out optical simulation of said detected error site of a pitch to output light intensity; and generating and providing a contour according to said output light intensity.

2. A mask pattern verification method comprising the steps of:

generating layout data from semiconductor circuit data;

detecting an error site of a hole of said generated layout data from a position relationship with an adjacent pattern;

carrying out optical simulation on said detected error site of a hole to output light intensity; and generating and providing a contour according to said output light intensity.

3. A mask pattern verification method comprising the steps of:

generating layout data from semiconductor circuit data;

carrying out optical simulation on said generated layout data to output light intensity;

generating and providing a contour according to said output light intensity;

verifying a distortion of said output contour according to said generated layout data; and correcting said layout data according to said verification result.

* * * * *